United States Patent
Williams et al.

(10) Patent No.: US 7,910,574 B2
(45) Date of Patent: Mar. 22, 2011

(54) TREATMENTS FOR THE CONTROL OF SCHISTOSOMIASIS

(75) Inventors: David L. Williams, Normal, IL (US); Ahmed Sayed, Normal, IL (US)

(73) Assignee: Illinois State University, Normal, IL (US)

( * ) Notice: Subject to any disclaimer, the term of this patent is extended or adjusted under 35 U.S.C. 154(b) by 307 days.

(21) Appl. No.: 12/001,404

(22) Filed: Dec. 11, 2007

(65) Prior Publication Data

US 2009/0149515 A1    Jun. 11, 2009

(51) Int. Cl.
- *A61K 31/41* (2006.01)
- *A61K 31/4166* (2006.01)
- *A61K 31/04* (2006.01)
- *A61K 31/33* (2006.01)

(52) U.S. Cl. ......... 514/183; 514/364; 514/741; 514/742

(58) Field of Classification Search .................. 514/364
See application file for complete search history.

(56) References Cited

U.S. PATENT DOCUMENTS

| | | |
|---|---|---|
| 6,207,855 B1 | 3/2001 | Toone et al. |
| 2003/0207815 A1 | 11/2003 | Stamler et al. |
| 2006/0287396 A1 | 12/2006 | Stevens et al. |

OTHER PUBLICATIONS

Definition of "silencing", Merriam-Webster's Medical Desk Dictionary at Merriam-Webster Online, 2005, downloaded from "http://www.merriam-webster.com/medical/silence", p. 1 of 1.*
Alger et al., Molecular & Biochemical Parasitology, 2002, vol. 121, pp. 129-139.*
Cenas et al., "Interactions of Nitroaromatic Compounds with the Mammalian Selenoprotein Thioredoxin Reductase and the Relation to Induction of Apoptosis in Human Cancer Cells," Journal of Biological Chemistry, vol. 281 (9), pp. 5593-5603 (Mar. 3, 2006).
Cerecetto et al., "Pharmacological Properties of Furoxans and Benzofuroxans: Recent Developments," Mini-Reviews in MEdicial Chemistry, vol. 5 (1), pp. 57-71 (Jan. 2005).
Kuntz et al., "Thioredoxin Glutathione Reductase from Shistosoma mansoni: An Essential Parasite Enzyme and a Key Drug Target," PLoS Medicine, vol. 4(6), pp. 1071-1086 (Jun. 2007).

* cited by examiner

*Primary Examiner* — James D Anderson
*Assistant Examiner* — Gregg Polansky
(74) *Attorney, Agent, or Firm* — Drinker Biddle & Reath LLP

(57) ABSTRACT

A method for controlling schistosome parasites in a mammal comprising delivering an effective amount of an agent for silencing TGR activity in the parasites.

1 Claim, 4 Drawing Sheets

TREATMENTS FOR THE CONTROL OF SCHISTOSOMIASIS

STATEMENT REGARDING FEDERALLY SPONSORED RESEARCH AND DEVELOPMENT

This work was supported in part by NIH/NIMH grant R03MH076449 (DLW) and by NIH/NIAID grant R01AI065622 (DLW).

FIELD OF THE INVENTION

This invention pertains to new treatments for schistosomiasis.

BACKGROUND OF THE INVENTION

Schistosomiasis is a chronic disease caused by trematode flatworms of the genus *Schistosoma*. The disease remains a major neglected, poverty-related health problem in many tropical areas. It is estimated that more than 200 million people are infected with schistosomiasis, resulting in 280,000 deaths annually while more than 20 million infected individuals experience high morbidity.

Currently chemotherapy is the main schistosomiasis control method and is mediated largely through the use of praziquantel (PZQ). The low cost of the drug and its efficacy against adult worms of all schistosome species that infect humans has lead to its very widespread use; currently tens of millions receive annual treatments of PZQ. However, because of high reinfection rates, PZQ must be administered on an annual or semi-annual basis.

There is a danger that widespread reliance on a single drug for schistosomiasis control will hasten the selection of drug-resistant parasites. In fact, twelve PZQ resistant isolates of *Schistosoma mansoni* have been obtained from schistosomiasis patients in Egypt. Four of the PZQ chemotherapy resistant parasites were accredited to host factors while eight of these isolates were implicated to be worm factors. There are also reports of *S. haematobium* patients who continued to pass eggs after at least two PZQ treatments. Moreover, PZQ resistant parasites have been selected for in the laboratory.

Artemether has shown promise as a new drug for schistosomiasis, although its use for schistosomiasis may be restricted in areas of malaria transmission so that its use as an antimalarial is not put at risk. Oxamniquine, a single dose anthelmintic drug is effective only against *S. mansoni* and resistance to oxamniquine has been reported further reducing its potential value in schistosomiasis control. The dependence on a single drug for the treatment of schistosomiasis is not sustainable; there is an urgent need for new drugs and drug targets for schistosomiasis treatment.

Schistosome parasites have a complex lifecycle involving snail intermediate and human definitive hosts. Humans become infected when contacting water containing cercariae released by infected snails. After penetration, cercariae remain in the skin for several days, then enter the general circulation and are carried to the lungs, where they reside for several further days before finally entering the liver. Once in the liver, parasites undergo rapid growth, development and sexual differentiation and locate a mate. After pairing, adult parasites migrate to the mesenteric venules (*S. mansoni* and *S. japonicum*) or the venules of the urogenital system (*S. haematobium*) of their human host where they commence egg production.

BRIEF SUMMARY OF THE INVENTION

Because schistosome parasites reside in an aerobic environment in their mammalian hosts they must have means to minimize damage from oxygen radicals (superoxide, $H_2O_2$, hydroxyl radical) produced by their own aerobic respiration as well as by the host immune assault. Schistosomes completely lack catalase and have minimal glutathione peroxidase activity, two enzymes involved in the reduction of $H_2O_2$. Defense against oxidative stress in schistosomes relies mainly on the activity of peroxiredoxins (Prx), a relatively recently described class of thiol-dependent peroxidases. Silencing of schistosome Prx expression by RNA interference leads to rapid parasite death, indicating that they are essential parasite proteins. The activity of schistosome peroxiredoxins is supported by cellular thiol reducing agents, either the tripeptide glutathione (GSH) or the 12 kDa protein thioredoxin.

In most eukaryotes there are two largely independent systems to detoxify reactive oxygen species, one based on GSH and the other based on thioredoxin. Each of these systems has a dedicated NADPH-dependent flavoenzyme to maintain GSH or thioredoxin in the reduced state, GSH reductase and thioredoxin reductase, respectively. However, our biochemical and genomic analyses have established that these two pathways in *S. mansoni* are dependent on a single, multifunctional selenocysteine-containing flavoenzyme, thioredoxin-glutathione reductase (TGR), which replaces both glutathione reductase and thioredoxin reductase in the parasite. Thus the parasite's redox system is subject to a bottleneck dependence on TGR and TGR is essential for survival of this parasite. Schistosome TGR is biochemically distinct from host enzymes and appears to be a molecular target of potassium antimonyl tartrate, which was used for schistosomiasis therapy for nearly 70 years. It is unknown at this time, however, whether potassium antimonyl tartrate functions through inhibition of TGR. Thus, in accordance with the present invention we identified *Schistosoma mansoni* TGR as the drug target to control schistosomiasis. We also validated the effectiveness of TGR targeting on parasite survival by both genetic and chemical means.

In its broadest sense, this invention therefore focuses on the parasite redox pathway and comprises the control of schistosomiasis by inhibiting TGR activity. It also comprises the use of selected oxadiazoles for this purpose as listed in Table 1 below.

TABLE 1

Structure and Potency of Oxadiazole 2-Oxides Used in this Study. The potency ($IC_{50}$ in μM) of the compounds against the glutathione reductase (GSSG) and thioredoxin reductase ($Trx(S)_2$) activities of *Schistosoma mansoni* thioredoxin glutathione reductase are as indicated. $IC_{50}$ values greater than 50 μM signify lack of fitted curve through the dose-response data, i.e. flat respnse within the range tested.

| | Analogue # | $R_1$ | $R_2$ | GSSG | $Trx(S)_2$ |
|---|---|---|---|---|---|
| Oxadiazole 2-oxide | 5 | 2-acetylfuran | 2-acetylfuran | 0.082 | 0.038 |
| | 6 | 1,3-dimethyl-1H-pyrazol-4-yl methyl ketone | 1,3-dimethyl-1H-pyrazol-4-yl methyl ketone | 4.08 | 1.29 |
| | 7 | 2-acetylthiophene | 2-acetylthiophene | 0.51 | 0.042 |
| | 8 | 4'-methoxyacetophenone | 4'-methoxyacetophenone | 2.44 | 0.105 |
| Furoxan | 9 | —CN | —Ph | 0.32 | 1.67 |
| | 10 | NA | NA | 12.5 | 6.68 |

In preliminary results on parasite cultured worms, these oxadiazoles kill adult worms at 5 μM concentration after 5 days. However, since the in vivo effect of these drugs on *S. mansoni* infected mice and larger mammals (e.g., humans) cannot be predicted because of differences in their bioavailability and toxicity actual effective treatment dosages will have to be determined using conventional known techniques. Also, treatment may be administered by injection or orally, with oral administration being preferred for treatment of humans.

BRIEF DESCRIPTION OF THE DRAWINGS

The accompanying drawings provide data in support of the invention as follows.

DETAILED DESCRIPTION OF THE INVENTION

The oxadiazole, 4-phenyl-3-furoxan-carbonitrile (also identified as furoxan or 2-oxido-4-phenyl-1-oxa-5-aza-2-azoniacyclopenta-2,4-diene-3-carbonitrile; SID: 24278622; CID: 1756; RVC-589), was found to be particularly effective in controlling schistosomiasis. Furoxan exhibits time-dependent irreversible inhibition of TGR through the release of NO. Furoxan inhibition of TGR is partially reversible, however, by strong thiol reducing agents, suggesting that the inhibition of TGR is through the modification of cysteine or selenocysteine residue(s) in the protein. The effects of four compounds belonging to the phosphinic amide series were also tested against freshly cultured *S. mansoni* worms. Out of the four tested compounds, compound 3 (N-benzothiazol-2-yl-phenyl-phosphoryl)-1,3-thiazol-2-amine, (NBPPTA)) was found to effectively kill the worms at 25 µM and 50 µM in 96 hrs and 24 hrs respectively.

TGR Inhibition of Cultured Worms

We also examined whether furoxan affected the survival of axenically cultured adult *S. mansoni* worms. Furoxan was found to be active against worms: 10 µM furoxan resulted in 100% parasite death within 24 hr and concentrations as low as 2 µM killed worms in 120 hr.

Nitric Oxide Production

Because oxadiazoles are known to release nitric oxide (NO) at physiological levels of thiols, we examined if NO release played a part in their mechanism of action (TGR inhibition and worm killing). First, all oxadiazoles that we examined produced NO at approximately the same amount when incubated in 5 mM cysteine, indicating that all are capable of NO production. The NO releasing capability of oxadiazoles was next tested with recombinant *S. mansoni* TGR enzyme with and without NADPH. Of the five oxadiazoles that we examined, furoxan showed the greatest release of NO (10× more/+NADPH, 3× more/−NADPH) compared with the other oxadiazoles that we tested (P<0.05). Unlike, other tested oxadiazoles, furoxan showed a greater NO release in the presence of NADPH than in its absence, suggesting that a possible enzymatic mechanism in NO release by furoxan with the parasite TGR.

Since furoxan was both the most efficient NO generator in the presence of TGR and was more active against cultured worms than the other oxadiazoles, we hypothesized that NO production may be involved in action of furoxan against cultured worms. To investigate this hypothesis we cultured adult *S. mansoni* worms with 100 µM carboxy-PTIO in the presence or absence of 10 µM of furoxan. Carboxy-PTIO is member of nitronyl nitroxide family reacts with NO to form the corresponding imino nitroxides and hence acts as a specific tool for NO purging and scavenging. We found that worm viability in the presence of furoxan with the NO scavenger was extended and similar to those seen for worms cultured with the other oxadiazoles, which presumably do not generate NO to the same extent as furoxan under the culture conditions.

Action of Inhibitors on Cultured Worms

Figure 2A:
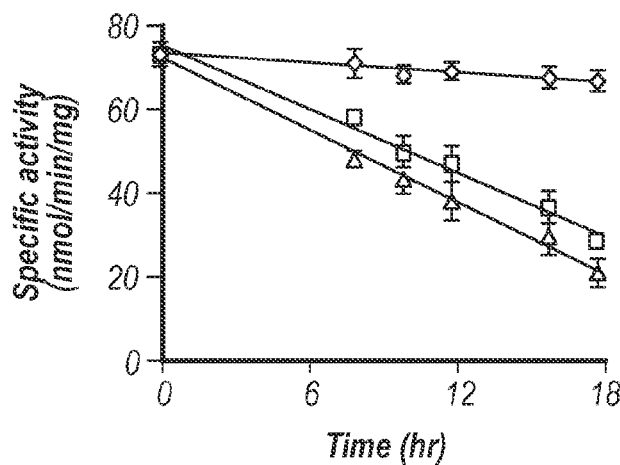
FIG. 2 is a series of graphs showing the action of compounds 3 and 9 on TGR activities in cultured *Schistosoma mansoni* worms as follows: (a) the specific thioredoxin reductase activity of TGR in worm homogenates from control worms (◇), 50 μM 3 treated worms (□), and 10 μM 9 treated worms (Δ), (b) the specific glutathione reductase activity of TGR in worm homogenate from control worms (◇), 50 μM 3 treated worms (□), and 10 μM 9 treated worms (Δ), and (c) the specific activity of lactate dehydrogenase in worm homogenates from control worms (◇), 50 μM 3 treated worms (□), and 10 μM 9 treated worms (Δ). The error bars represent ±standard deviation from the average of three independent experiments.
Figure 2B:
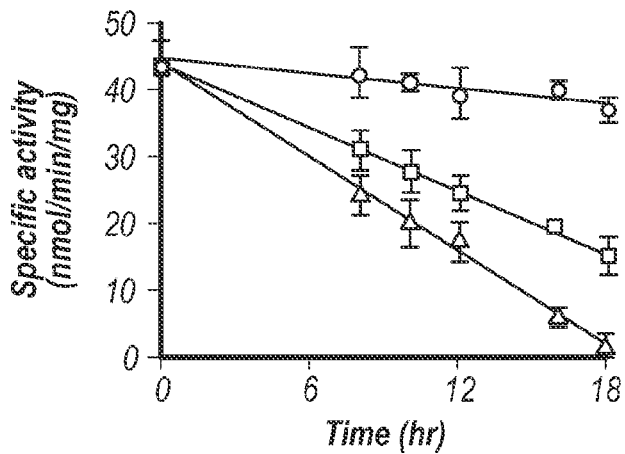
Figure 2C:
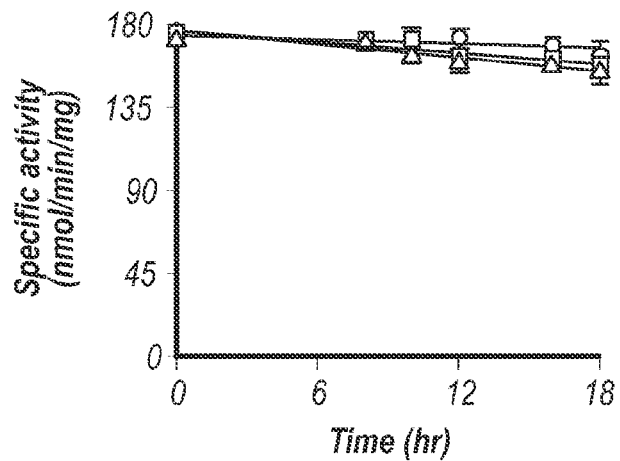

Because both furoxan inhibits recombinant parasite TGR and causes rapid death of cultured parasites, we examined if the mechanism of action of this compound in living worms was through, at least in part, inhibition of TGR activity. Freshly perfused adult *S. mansoni* worms were cultured with 10 µM furoxan or 50 µM NBPPTA. The parasites were observed for viability and collected at different time points. Because parasite TGR is a multifunctional enzyme and possesses both thioredoxin reductase and glutathione reductase activities both activities were determined at each time point. The activity of lactate dehydrogenase was monitored as a control enzyme. After 18 hrs treatment both furoxan and NBPPTA dramatically reduced thioredoxin reductase and GSH reductase activity of the parasite TGR compared to carrier treated-control worms (83% and 93% for furoxan (FIGS. 2a, 2b) and 69% and 59% (FIGS. 2a, 2b) for NBPPTA. The activity of parasite lactate dehydrogenase in homogenates from furoxan-treated worm showed no significant change from carrier only treated worms (FIG. 2c).

Drug Cytotoxicity Screening

To examine if furoxan is tolerated by mammalian cells, we incubated the murine myeloma cell line SP2/0 with the drugs at given concentrations and monitored cell viability at 24 hr and 120 hr. At 120 hr in 2 µM furoxan ~25% mortality of myeloma cells was observed compared to 100% mortality of adult *S. mansoni* worms at the same concentration. Myeloma cells tolerated furoxan at concentrations as high as 100 µM. Differential cytotoxicity of furoxan on the worm survival and myeloma cells were also seen after 24 hrs of drug application.

In Vivo Action of Furoxan against Schistosome Infections

Figure 3A:
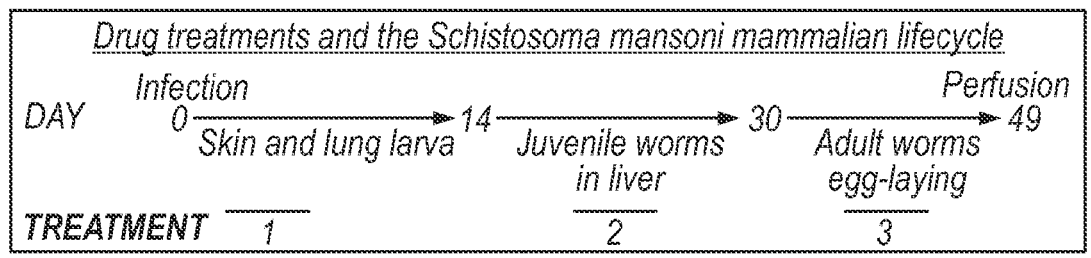
FIG. 3 relates to in vivo drug treatment with compound 9, with (a) administration of compound 9 at 10 mg/kg for 5 days at different points during the development of *Schistosoma mansoni* in the mouse, (b) the effect on adult worm burdens after treatment of *S. mansoni* infected mice with compound 9 in treatment 1 (▲, skin-stage parasites, n=8), treatment 2 (■, juvenile liver-stage parasites, n=8), treatment 3 (□, Adult egg-laying parasites, n=8); drug carrier treated control infected mice (♦, n=16) where points represent data from individual mice; * P<0.0001, and the horizontal bars represent the average point of each treatment, (c) anti-pathology effects of treatment with compound 9, with liver (closed symbols) and spleen (open symbols) weights from infected control mice (I, ♦), treatment 1 (1, ■), treatment 2 (2, ▲) and uninfected age matched control mice (U, ●); * P<0.0001, and (d) relative efficacy of compound 9 (-♦-), praziquantel (-■-) and artemether (-▲-) against *S. mansoni* infections in mice.
Figure 3B:
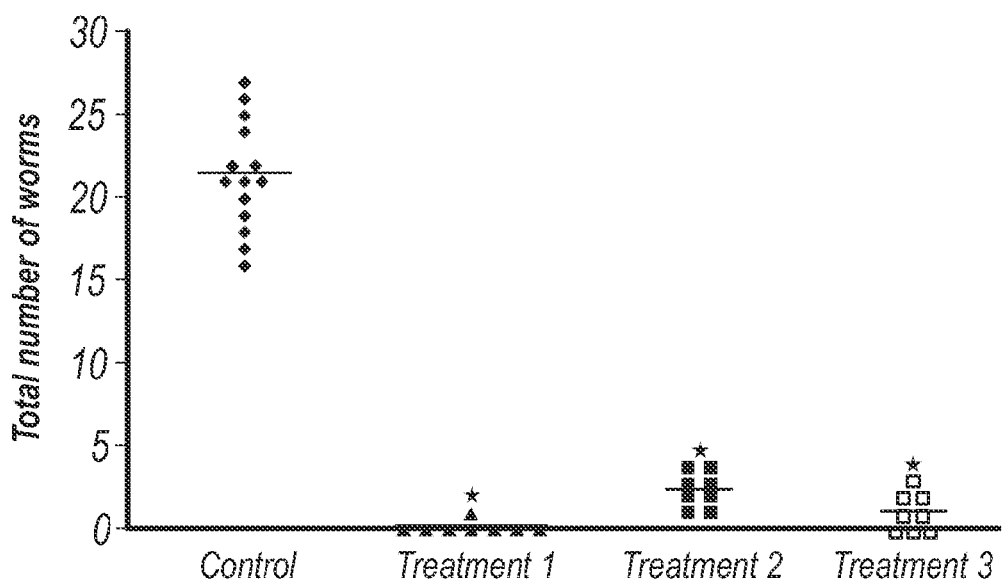
Figure 3C:
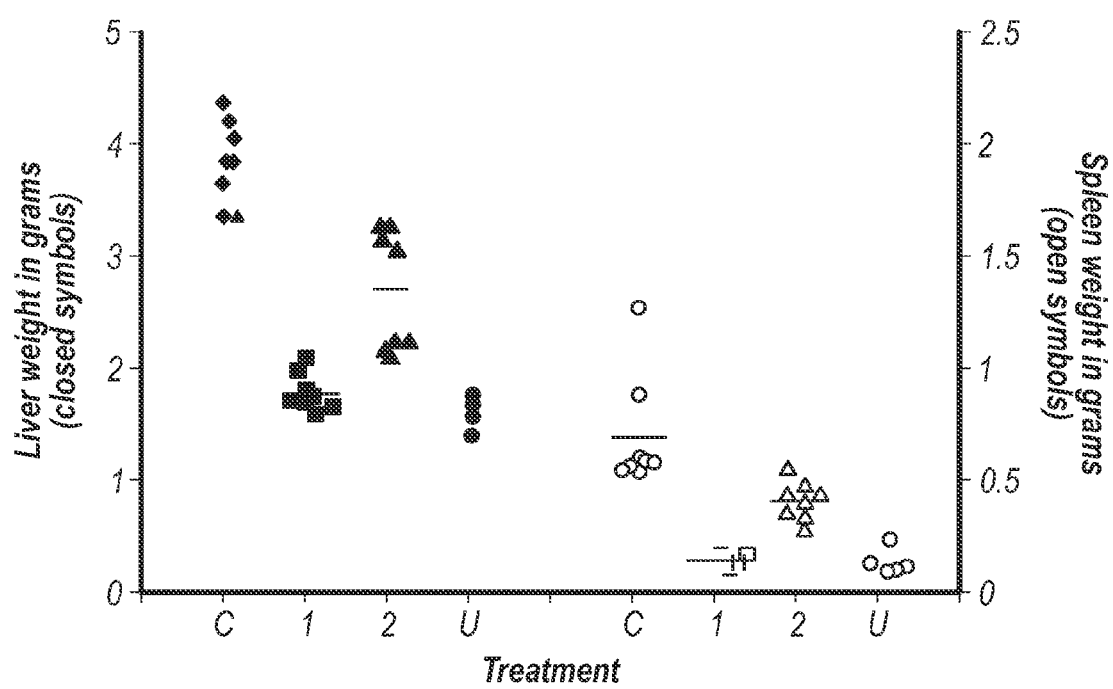

To determine if furoxan was active against schistosome infections, its efficacy against different parasite life stages in an experimental mammalian host was determined. In all treatments furoxan was administrated once daily for 5 consecutive days by intraperitoneal injection at 10 mg/kg to *S. mansoni* infected mice; treatment 1 started one day after infection (skin stage parasites), treatment 2 started 23 days after infection (juvenile, liver-stage parasites), and treatment 3 started at day 37 days after infection (adult, egg laying parasites in the mesenteric system) (FIG. 3a). In all treatments adult worms were quantified after perfusion of mice 49 days post infection. In all experimental treatments large and highly significant reductions in worm burdens were observed. Treatment 1 resulted in decrease in worm burden of >99% (P<0.0001) compared to the control *S. mansoni* infected mice (FIG. 3b). The protective effect of furoxan was also seen in the reduction of hepatomegaly (P<0.0001) compared to control infected mice; indeed the weights of the livers in this treatment were not statistically different from livers from uninfected age-matched mice (P>0.1) and showed no signs of egg granulomas. Treatment 2 resulted in a highly significant decrease of 89% (P<0.0001) in worm burdens (FIG. 3b) and dramatic reductions in hepato- and splenomegaly relative to control infected mice (P<0.0001) (FIG. 3c). The number of liver granulomas was also considerably reduced compared to the control infections. Moreover, the worms recovered were distinctly smaller after this treatment, especially male worms. An equal number of male and female worms were recovered from this treatment indicating that furoxan was equally active against both sexes. Treatment 3 resulted in a highly significant decrease of 94% (P<0.0001) in worm burdens relative to control infected mice (FIG. 3b). The livers collected from treatment exhibited a greatly reduced number of egg-induced granulomas compared to the control group and dramatic reduction in hepatomegaly (P<0.0001).

Summary of Results

Furoxan is a heterocyclic compound that shares with other members of the its family a 1,2,5-oxadiazole ring. Furoxan has the ability to release nitric oxide in the presence of thiol cofactors at physiological pH. The parasite TGR is equipped with five cysteines and one selenocysteine that may act as thiol reactive centers not only with furoxan but also with its homologous structures of the oxadiazoles family (Table 1).

Evidence that the anthelminthic effects of the compounds of Table 1 due to the inhibition of TGR is evident from the results in FIG. 2. The death of treated cultured worms is preceded by the inhibition of the GR and TrxR activities of TGR. No inhibition of an abundant enzyme LDH was seen.

The activity of furoxan significantly surpasses criteria established by the World Health Organization Special Programme for Research and Training in Tropical Disease (WHO/TDR) for potential lead compounds. The activity criteria for hits and leads for schistosomiasis are 100% inhibition of motility of adult parasites at 5 μg/ml ('hits') and that they should be active when given ip or sc in 10% DMSO in 5 injections at 100 mg/kg, with 80% reduction in worm burdens being a highly active lead compound. Furoxan at 1.87 μg/ml produces 100% inhibition of motility of adult parasites in 24 hr and concentrations as low as 0.38 μg/ml are active at longer times. All trials in mice resulted in at least an 89% reduction in worm burdens when furoxan was administered at 10 mg/kg, or 1/10 the maximum recommended dosage.

Figure 3D:
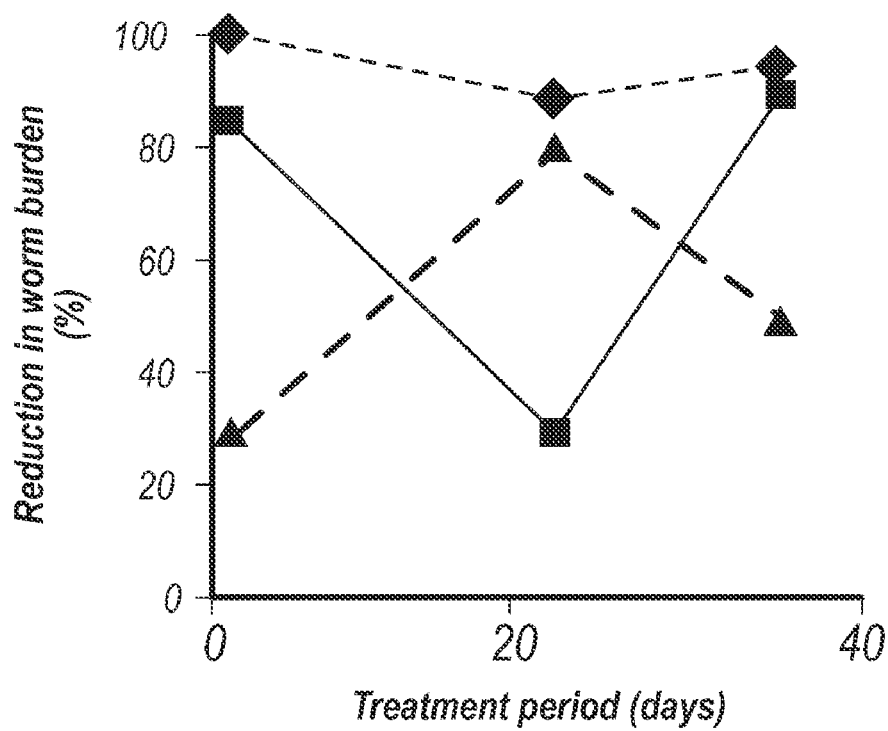

It is significant to note that our results indicate that furoxan is highly active against all intra-mammalian lifecycle stages of S. mansoni, with at least an 89% reduction in worm burdens regardless of the lifecycle stage present during the treatment. Neither PZQ nor ART display such broad activity. Furoxan is particularly active against early stages of the infection as only one adult parasite was recovered from the eight mice infected. The efficacy of furoxan is equal to or better than PZQ and ART in the mouse model reported in previous studies (FIG. 3d). These studies indicate that PZQ is much less effective against juvenile liver parasites than against adult parasites, with only a 25-30% reduction in worm burdens. Although artemether (an artemisinin derivative) affords ~80% reduction if juvenile parasites are targeted, it is less effective against adult schistosome parasites, resulting in less than 50% reduction in worm burden. Therefore, furoxan could be useful as a prophylactic treatment (it is effective skin and migrating parasites) and would kill adult parasites, which trigger disease by egg production and are typically the diagnostic stage.

Test Procedures

1. Parasite Preparation

Schistosome life stages used in this research were supplied in part by the National Institute of Allergy and Infectious Diseases Schistosomiasis Resource Center at the Biomedical Research Institute (Rockville, Md., United States) through NIAID Contract N01-AI-30026. Mice (NIH-Swiss) were infected by percutaneous tail exposure for 2 hrs to 60 S. mansoni cercariae (NMRI strain) for in vivo studies or 180 cercariae to obtain adult parasites for in vitro studies. Adult S. mansoni worms were obtained from 7-week infected mice by perfusion with RPMI1640 media. The worms were collected and washed at least twice with fresh media and incubated for 1 hr at 37° C. in 5% $CO_2$ incubator before any in vitro drug treatments were conducted. This study was approved by the Institutional Animal Care and Use Committee of Illinois State University May 2006; DHHS animal welfare assurance number A3762-01).

2. Enzyme Assays

Enzyme assays were performed at 25° C. in 0.1 M potassium phosphate, pH 7.4, 10 mM EDTA. Thioredoxin reductase activity of TGR was determined using either 3 mM 5,5' dithiobis(2-nitrobenzoic acid) (DTNB, Ellman's reagent) or 16 μM recombinant S. mansoni thioredoxin-1 (Alger et al 2002). One enzyme unit was defined as the NADPH-dependent production of 2 μmol of 2-nitro-5-thiobenzoic acid per minute using $\epsilon_{412\,nm}=13.6$ mM$^{-1}$ cm$^{-1}$ or the consumption of 1 μmol of NADPH ($\epsilon_{340\,nm}=6.22$ mM$^{-1}$ cm$^{-1}$) during the first three minutes. Glutathione reductase activity was determined with 100 μM GSH disulfide and 100 μM NADPH by measuring the decrease in $A_{340\,nm}$ due to consumption of NADPH ($\epsilon_{340\,nm}=6.22$ mM$^{-1}$ cm$^{-1}$) during the first three minutes. Activity of the control enzyme lactate dehydrogenase (LDH) was determined with 10 μM sodium pyruvate and 100 μM NADPH. Each assay was done in triplicate and each experiment was repeated three times.

3. Inhibitor Studies on Cultured Worms

Compounds were dissolved in dimethylsulfoxide (DMSO) and added at concentrations indicated to freshly perfused worms in RPMI1640 containing 25 mM Hepes, pH 7, 150 units/ml penicillin, 125 μg/ml streptomycin, and 10% fetal calf serum (Cell Grow, Fisher). The media were replaced every two days with fresh media with addition of the compounds at the designated concentrations. Control worms were treated with equal amounts of DMSO alone. Worms were subsequently observed for motility, and mortality and collected at the indicated times for analysis. Worms were homogenized by sonication in PBS and homogenates were assayed for enzyme activities as described. To access the importance of NO production the potassium salt of the compound 2-(4-carboxyphenyl-4,4,5,5,-tetramethylimidazoline-1-oxyl 3-oxide (carboxy-PTIO, Invitrogen), an NO scavenger, was dissolved in water and incubated with freshly perfused S. mansoni worms as described at 100 μM in the presence or absence of 10 μM furoxan.

4. In Vivo Drug Treatments

Furoxan was dissolved in DMSO and administrated by intraperitoneal injection to S. mansoni infected mice (NIH-Swiss, National Cancer Institute) at 10 mg/kg once a day for 5 consecutive days following the schedule in (FIG. 3a). Furoxan at this dosage has been shown previously to be well tolerated by mice (Aguirre 2006). The control S. mansoni infected mice were administrated a corresponding amount of the drug carrier on the same timetable. Age-matched uninfected mice were used as reference group.

5. Cytotoxicity Assay

Cytotoxicity assays were performed using sulforhodamine B to determine cellular protein content. Murine myeloma cell line SP2/0 was cultured in 96-well microtiter plates containing 0.2 ml of RPMI-1640 per well at a cell density of 900 per well at 37° C. in 5% $CO_2$. Cells were treated with drug concentrations (or drug carrier alone) for times as indicated. After treatment, cells were fixed with 10% TCA at 4° C. for 1 hr. Fixed cells were rinsed to remove fixative and then stained in 0.4% (wt/vol) sulforhodamine B (Sigma) in 1% acetic acid for 35 min. After washing with 1% acetic acid and dye extraction in 10 mM Tris (pH 10.5), plates were read at $A_{564\,nm}$. The $A_{564\,nm}$ of drug-treated cells was compared to carrier-only-treated cells.

6. Determination of NO Release

NO release by different oxadiazoles was determined by 2,2'-azino-bis(3-ethylbenzthiazoline-6-sulphonic acid)

[ABTS, Sigma] oxidation method [Nims et al, Methods 7, 48-54; 1995]. Different oxadiazoles at 10 µM were incubated at RT for 50 minutes with 15 nM recombinant SmTGR in the presence or absence of 100 µM NADPH. The (oxadiazole+ SmTGR/±NADPH) mixture was then added to an aerobic PBS, pH 7.4, containing 5 mM ABTS. The absorbance of the resulting green ABTS$^+$ were measured at $A_{660}$. A conversion factor was calculated to adjust the readings from 1 ml reaction to 96-well plate. The concentrations of the released NO were calculated as a percentage of the added oxadiazoles. Each reaction was done in triplicate and the data is the average of three independent experiments. The conversion factor from 1 ml reaction to 96-well plate was performed by plotting the oxidized form of ABTS (ABTS$^+$) from the reduced form ABTS (ABTS$^+$-ABTS) versus different concentration of tested ABTS. The slope of the regression line was calculated and used to recalculate the data at $A_{660}$ in 200 µl reaction [Nims et al, Methods 7, 48-54; 1995].

7. Statistical Analysis

The statistical significance of worm burden, hepatomegaly, and splenomegaly reduction between Fx treated parasites compared to the control group was determined by two-tailed Student's T test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What we claim is:

1. A method for controlling schistosome parasites in a mammal in need thereof comprising:
    delivering to a said mammal an effective amount of 4-phenyl-3-furoxan-carbonitrile for inhibiting thioredoxin-glutathione reductase (TGR) activity in said parasites.

* * * * *